(12) United States Patent
Levin et al.

(10) Patent No.: US 9,120,377 B2
(45) Date of Patent: Sep. 1, 2015

(54) METHOD, SYSTEM AND COMPUTER READABLE MEDIUM EMBODYING A COMPUTER PROGRAM PRODUCT FOR DETERMINING A VEHICLE OPERATOR'S EXPECTATION OF A STATE OF AN OBJECT

(75) Inventors: Daniel Levin, Göteborg (SE); Gustav Markkula, Göteborg (SE)

(73) Assignees: VOLVO CAR CORPORATION, Gothenburg (SE); VOLVO TECHNOLOGY CORPORATION, Gothenburg (SE)

( * ) Notice: Subject to any disclaimer, the term of this patent is extended or adjusted under 35 U.S.C. 154(b) by 389 days.

(21) Appl. No.: 13/591,890

(22) Filed: Aug. 22, 2012

(65) Prior Publication Data

US 2013/0058536 A1  Mar. 7, 2013

(30) Foreign Application Priority Data

Sep. 2, 2011 (EP) ...................................... 11179802

(51) Int. Cl.

| | |
|---|---|
| *G06K 9/80* | (2006.01) |
| *B60K 28/06* | (2006.01) |
| *A61B 5/18* | (2006.01) |
| *G08G 1/16* | (2006.01) |
| *A61B 5/00* | (2006.01) |
| *A61B 5/11* | (2006.01) |

(52) U.S. Cl.
CPC ................ *B60K 28/066* (2013.01); *A61B 5/18* (2013.01); *G08G 1/168* (2013.01); *A61B 5/1128* (2013.01); *A61B 5/6893* (2013.01); *B60W 2540/22* (2013.01)

(58) Field of Classification Search
None
See application file for complete search history.

(56) References Cited

FOREIGN PATENT DOCUMENTS

WO WO-2008/032220 A2 3/2008

OTHER PUBLICATIONS

European Search Report dated Feb. 22, 2012 for European Patent Application No. 11179802.1.

*Primary Examiner* — Stephen R Koziol
*Assistant Examiner* — Raphael Schwartz
(74) *Attorney, Agent, or Firm* — Harness, Dickey & Pierce, P.L.C.

(57) ABSTRACT

The present invention generally relates to a method, a system and/or a computer readable program. An embodiment of the method includes acquiring an input signal indicative of the operator's expectation of the state of the object at a first point in time; determining a state of the object at a second later point in time based on the input signal; acquiring an input signal indicative of an estimated visual input of the operator at the second point in time; determining the operator's expectation of the state at the second point in time, based on the operator's expectation of the state of the object at the first point in time, and the estimated visual input and the state of the object at the second point in time; and providing an output signal indicative of the operator's expectation of the state at the second point in time.

12 Claims, 8 Drawing Sheets

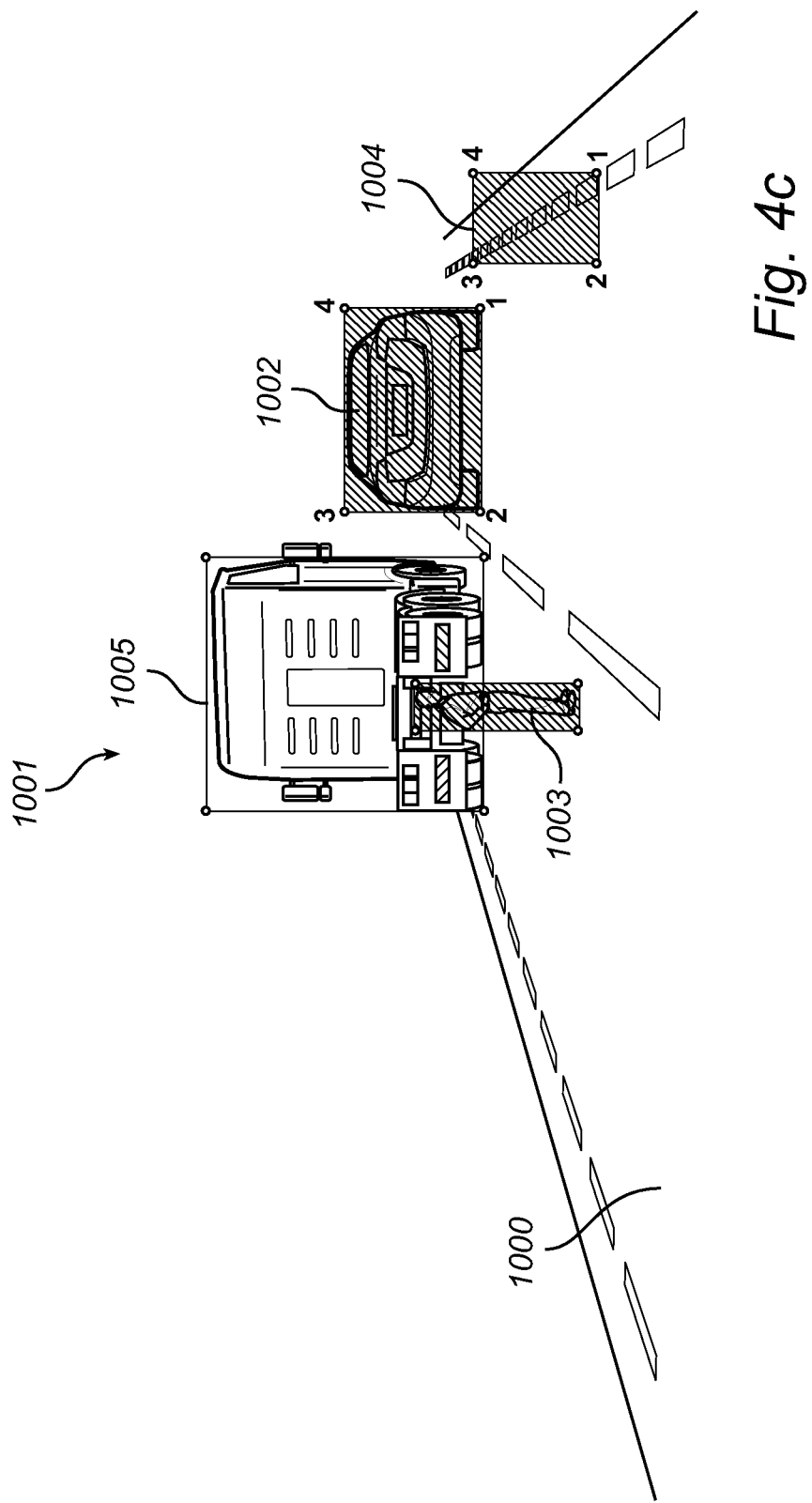

METHOD, SYSTEM AND COMPUTER READABLE MEDIUM EMBODYING A COMPUTER PROGRAM PRODUCT FOR DETERMINING A VEHICLE OPERATOR'S EXPECTATION OF A STATE OF AN OBJECT

PRIORITY STATEMENT

This claims priority under 35 U.S.C. §119 to European Patent Application No. 11179802.1, filed on Sep. 2, 2011, the contents of each of which are hereby incorporated by reference in their entirety.

TECHNICAL FIELD

The present invention relates to a method for determining a vehicle operator's expectation of a state of an object in the operator's environment.

The present invention also relates to a corresponding system and computer readable medium for embodying a computer program product for determining a vehicle operator's expectation of a state of an object in the operator's environment.

BACKGROUND OF THE INVENTION

Traffic accidents often occur due to the driver not being aware of the surrounding traffic situation. In order to prevent accidents caused by the driver not being aware of the surrounding traffic situation, it may be vital to provide the driver with a warning message to re-establish the attention of the driver to the surrounding traffic situation. However, it is also crucial that a warning system does not warn in situations where the driver is aware of the surrounding traffic situation since such a warning system may cause information overload to the driver, and reduce the level of trust the driver has with regard to the warnings.

Hence, there exist a need for a system, a method and a computer readable medium embodying a computer program product that provides input data to e.g. the different warning systems in vehicles, so that they only warn in situations where it is needed.

SUMMARY OF THE INVENTION

According to a first aspect of the present invention, the above may be met by a method for determining a vehicle operator's expectation of a state of an object in the operator's environment is provided. The method comprises acquiring an input signal indicative of the operator's expectation of the state of the object at a first point in time; determining a state of the object at a second point in time based on an input signal indicative of the object's state, the second point in time being later than the first point in time; acquiring an input signal indicative of an estimated visual input of the operator at the second point in time; determining the operator's expectation of the state of the object at the second point in time, based on the operator's expectation of the state of the object at the first point in time, the estimated visual input of the operator of the vehicle at the second point in time and the state of the object at the second point in time; providing an output signal indicative of the operator's expectation of the state of the object at the second point in time.

According to a third aspect of the present invention, the above may be met by a system for determining a vehicle operator's expectation of a state of an object in the vehicle operator's environment is provided. The system comprises: means for acquiring an input signal indicative of the operator's expectation of the state of the object at a first point in time; means for determining a state of the object at a second point in time based on an input signal indicative of the object's state, the second point in time being later than the first point in time; means for acquiring an input signal indicative of an estimated visual input of the operator at the second point in time; means for determining the operator's expectation of the state of the object at the second point in time, based on the operator's expectation of the state of the object at the first point in time, the estimated visual input of the operator of the vehicle at the second point in time and the state of the object at the second point in time; means for providing an output signal indicative of the operator's expectation of the state of the object at the second point in time.

A method according to the first aspect of the present invention and a system according to the third aspect of the present invention provides an output signal that may be used as input for e.g. the various warning systems that exist in vehicles today.

An object in the operator's environment may for example be, but is not limited to, other vehicles, pedestrians, animals, road signs, road borders and lane markings.

The input signal indicative of the operator's expectation of the state of the object at a first point in time corresponds to the output signal being provided as a result of the method and as an output signal from the system, from the previous time the method was executed or the system employed. Hence, the method is iterative and the operator's expectation of the state of the object is updated based on the operator's previous expectation of the state of the object, the operator's estimated visual input and the actual state of the object.

Any method which is capable of model-based tracking of the state of an object based on measurements that are imprecise, and sometimes missing altogether, can be used in order determine the operator's expectation of the state of the object at the second point in time, based on the operator's expectation of the state of the object at the first point in time, the estimated visual input of the operator of the vehicle at the second point in time and the state of the object at the second point in time. Many existing filtering algorithms can be suitable here, for example Kalman filters or particle filters, where varying levels of attention to an object can be taken into account by modulating the measurement noise assumed in the filter.

According to one exemplary embodiment, the time elapsed between the first point in time and the second point in time is preferably in the magnitude of hundredths or tenths parts of a second. It is for example conceivable to iterate the method twenty or forty times per second. The difference in time between the first and second point in time will then be a twentieth part of a second or a fortieth part of a second, respectively.

According to one exemplary embodiment of the first and third aspects of the present invention, the state of an object includes at least one of the position of the object, the movement of the object and the acceleration of the object.

According to this exemplary embodiment, the state of the object includes either the position of the object, the movement of the object or the acceleration of the object. It may also include a combination of the position of the object and the movement of the object, or the position of the object and the acceleration of the object, or the movement of the object and the acceleration of the object, or a combination of the position of the object, the movement of the object and the acceleration of the object.

According to one exemplary embodiment, the input signal indicative of the object's movement may be provided by the same means that provides an input signal indicative of the object's position.

According to one exemplary embodiment, the different elements, i.e. position, movement, acceleration, that may be comprised in the state of the object, may be treated simultaneously in the method and the system. However, according to one other exemplary embodiment, the different elements may be treated separately in the method and the system. Hence, according to this exemplary embodiment, different input signals may e.g. be provided for the different elements, or the operator's expectation of the movement of an object may be determined in one method step or in one means of the system and the operator's expectation of the position of the object may be determined in another method step or in another means in the system.

According to one exemplary embodiment, the object's current state and movement is determined in the X and Y directions of a coordinate system. According to one exemplary embodiment, the object is approximated as a 3D box with target corner points. According to one exemplary embodiment, the state may thereafter be calculated using the four object corners as input, whose mean define the center point of the object in each of the X and Y directions. According to one exemplary embodiment, the object's movement may be calculated by first calculating the corner point velocity for each of the individual corners and thereafter taking the mean.

According to one exemplary embodiment, it is possible to determine the operator's expectation of the movement of the object by deriving the operator's estimated position of the object. When discussing movement, it is meant to understand the relative movement between the object and the operator of the vehicle. Hence, all movements are considered in a coordinate system, with the operator of the vehicle in origin.

According to one exemplary embodiment, it is possible to determine the operator's expectation of the acceleration of the object by deriving the operator's estimated movement of the object. When discussing acceleration, it is meant to understand the relative acceleration between the object and the operator of the vehicle. Hence, all accelerations and movements are considered in a coordinate system, with the operator of the vehicle in origin.

According to one exemplary embodiment of the first aspect of the present invention, the input signal indicative of an estimated visual input of the operator at the second point in time is determined based on an input signal indicative of physiological data comprising information relating to at least one of eye, face and body motion of the operator of the vehicle.

According to one exemplary embodiment of the third aspect of the present invention, the system further comprises means for determining an estimated visual input of the operator at the second point in time, based on an input signal indicative of physiological data comprising information relating to at least one of eye, face and body motion of the operator of the vehicle.

The estimated visual input is determined by comparing the physiological data of the operator with a predetermined set of rules in order to estimate the operator's visual input of objects in the environment. It is for example conceivable to use rules defining the likeliness of sight direction depending on the operator's head and/or eye direction. It is also conceivable to apply rules relating to sight obstacles being present in the vehicle. Furthermore, it is also conceivable to apply rules relating to sight obstacles being present in the environment surrounding the vehicle.

According to one exemplary embodiment of the first aspect of the present invention, the method further comprises: determining a factor by which the operator's expectation of the state of the object at the first point in time and the state of the object at the second point in time should be weighed when determining the operator's expectation of the state of the object at the second point in time, wherein the factor is determined by comparing the operator's estimated visual input of the object at the second point in time with a predetermined set of rules.

According to one exemplary embodiment of the third aspect of the present invention, the system further comprises means for performing the method steps mentioned above for the exemplary embodiment of the first aspect of the present invention.

According to these exemplary embodiments of the first and third aspects of the present invention, the operator's expectation of the object's state is calculated by weighing together the operator's previous expectation of the object's state, i.e. the expectation at the first point in time, with the current real state of the object, i.e. the state of the object at the second point in time. The weighing factor is in this exemplary embodiment variable and depends on the driver's estimated visual input of the specific object. According to one exemplary embodiment, the weighing factor can vary between 0 and 1, according to the predetermined set of rules. If the operator gives the object much attention, a high weighing factor will be given and if the operator gives the object little attention a low weighing factor will be given.

According to one exemplary embodiment of the first and third aspects of the present invention, the input signal indicative of the operator's visual input is generated by means of an image sensor monitoring the operator. The image sensor monitoring the operator of the vehicle may for example be a camera.

According to one exemplary embodiment of the first and third aspects of the present invention, the input signal indicative of physiological data comprising information relating to at least one of eye, face and body motion of the operator of the vehicle is generated by means of an image sensor monitoring the operator. However, it is also conceivable with a plurality of sensors and/or cameras monitoring the operator of the vehicle.

According to one exemplary embodiment of the first and third aspects of the present invention, an input signal indicative of the state of an object is provided by means of a sensor. According to one exemplary embodiment, a plurality of sensors is being employed. According to these exemplary embodiments, the input signal indicative of an object's state may for example be provided by a sensor such as a camera or a radar. It is also conceivable to use a combination of e.g. a radar and a camera, or several radar sensor or cameras.

According to one exemplary embodiment of the first and third aspects of the present invention, an input signal indicative of the state of an object is provided by means of object-to-vehicle communication means. According to this exemplary embodiment, the input signal indicative of an object's state may for example be provided by means for vehicle-to-vehicle communication, means for pedestrian-to-vehicle communication, means for infrastructure-to-vehicle communication or e.g. means for road sign-to-vehicle communication or a combination of any or all of these means. Means for infrastructure-to-vehicle communication may e.g. be a base station located along, to the side of, or integrated in the road, or a satellite, etc.

According to one exemplary embodiment, the input signal indicative of the state of the object is provided by means of a combination of a sensor and means for object-to-vehicle communication. The input signal may not need to be provided in a similar manner for each of the different object types surrounding the vehicle. It is for example conceivable that the input signal indicative of the state of a vehicle in the surrounding is provided by means of vehicle-to-vehicle communication means, while the input signal indicative of the state of a pedestrian is provided by means of a sensor. Examples of communication means that may be employed are other vehicles, base stations located along, to the side of, or integrated in the road, or satellites, etc, which may be arranged to transmit e.g. information of position, velocity, acceleration, yaw rate, etc. Road sensors may also provide information of speed limits, road curvature, temperature, road friction properties, etc.

According to a second aspect of the present invention, a method for determining a vehicle operator's awareness of an object in the operator's environment at a second point in time is provided. The method comprises: determining the operator's expectation of the state of the object at the second point in time, based on an input signal indicative of the operator's expectation of the state of the object at the second point in time, wherein the input signal is provided by means of a method according to the first aspect of the present invention; determining the state of the object at the second point in time based on an input signal indicative of the object's state; comparing the operator's expectation of the state of the object at the second point in time with the state of the object at the second point in time; determining the difference between the operator's expectation of the state of the object at the second point in time with the state of the object at the second point in time; and providing an output signal indicative of the difference between the operator's expectation of the state of the object at the second point in time and the state of the object at the second point in time.

According to a fourth aspect of the present invention, a system for determining a vehicle operator's awareness of an object in the operator's environment at a second point in time is provided. The system comprises means for determining the operator's expectation of the state of the object at the second point in time, based on an input signal indicative of the operator's expectation of the state of the object at the second point in time, wherein the input signal is provided by means of a system according to the third aspect of the present invention; means for determining the state of the object at the second point in time based on an input signal indicative of the object's state; means for comparing the operator's expectation of the state of the object at the second point in time with the state of the object at the second point in time; means for determining the difference between the operator's expectation of the state of the object at the second point in time with the state of the object at the second point in time; and means for providing an output signal indicative of the difference between the operator's expectation of the state of the object at the second point in time and the state of the object at the second point in time.

A method according to the second aspect of the invention and a system according to the fourth aspect of the invention provide an output signal that may be used as input for e.g. the various warning systems that exists in vehicles today.

According to one exemplary embodiment of the second and fourth aspects of the present invention, the difference between the real state of the object and the operator's expectation of the state of the object is assessed by comparing the actual difference between reality and expectation. Hence, the difference in position may e.g. be expressed in meters, the difference in movement may e.g. be expressed in meters/ second and the difference in acceleration may e.g. be expressed in meters/second squared. According to one exemplary embodiment of the second and fourth aspects of the present invention, the difference between the real state of the object and the operator's expectation of the state of the object is assessed by calculating the percentage that the expectation differs from the reality.

According to a fifth aspect of the present invention, a computer readable medium embodying a computer program product for determining a vehicle operator's expectation of a state of an object in the operator's environment is provided, the computer program product comprising code configured to, when executed by a processor, acquiring an input signal indicative of the operator's expectation of the state of the object at a first point in time; determining a state of the object at a second point in time based on an input signal indicative of the object's state, the second point in time being later than the first point in time; acquiring an input signal indicative of an estimated visual input of the operator at the second point in time; determining the operator's expectation of the state of the object at the second point in time, based on the operator's expectation of the state of the object at the first point in time, the estimated visual input of the operator of the vehicle at the second point in time and the state of the object at the second point in time; and providing an output signal indicative of the difference between the operator's expectation of the state of the object at the second point in time and the state of the object at the second point in time. The computer program may further, according to various exemplifying embodiments, comprise code configured operate according to the method, and/or embodiments thereof, according to the present invention. The computer readable medium may be one of a removable nonvolatile random access memory, a hard disk drive, a floppy disk, a CD-ROM, a DVD-ROM, a USB memory, an SD memory card, or a similar computer readable medium known in the art.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing exemplary embodiments of the present invention, in which:

FIGS. 4a-c illustrates a side view, a top view and a driver's view, respectively, of objects appearing in the driver's environment.

DESCRIPTION OF EXEMPLARY EMBODIMENTS

Figure 1:
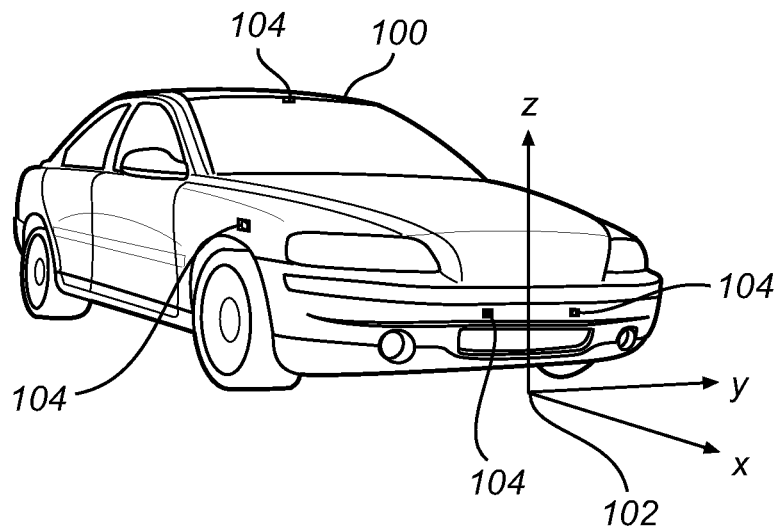
FIG. 1 is a perspective view of a vehicle equipped with external sensors and a coordinate system at its front end.

The present invention will now be described more fully hereinafter with reference to the accompanying drawings, in which exemplary embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

In the following, the present invention is described with reference to a system for determining a vehicle operator's expectation of a state of an object in the operator's environment. The vehicle is preferably equipped with interior sensor(s) for retrieving information of the vehicle operator and external sensor(s) for retrieving information of the vehicle operation as well as the surrounding environment of the vehicle. For the sake of better understanding, the internal and external sensors will now be described in relation to FIGS. 1-3.

FIG. 1 shows an exemplary vehicle, here illustrated as a car 100, in which a system according to the present invention may be incorporated. The car 100 is provided with external sensors 104 arranged to detect vehicle operation, such as overtaking, vehicle speed, vehicle yaw rate, etc, and the surrounding environment of the vehicle, e.g. lane markings, road marks, road curves, surrounding vehicles, pedestrians etc. The external sensors 104 may be e.g. cameras or radar sensors. Preferably, a combination of camera and radar sensors may be used, since the camera provides a high precision when determining the height and width of the object, whereas a radar sensor provides a high precision when determining the distance to the object. Hereby, size, position, speed, etc. of a surrounding object can be determined.

With reference to the position of the car 100, a coordinate system 102 is here illustrated as a Cartesian coordinate system located at the front end of the car 100. The coordinate system 102 is arranged to follow the vehicle and the axis represent the longitudinal direction (x-axis), lateral direction (y-axis) and vertical direction (z-axis), respectively. The detected objects, in conjunction with the coordinate system 102 of the car 100, are provided to a system of the vehicle such that the system can determine the size and position of the object relative to the car 100. As the system is continuously provided with the detected objects from the different sensors 104, it is also possible to determine speed and acceleration of surrounding traffic environment.

Figure 2:
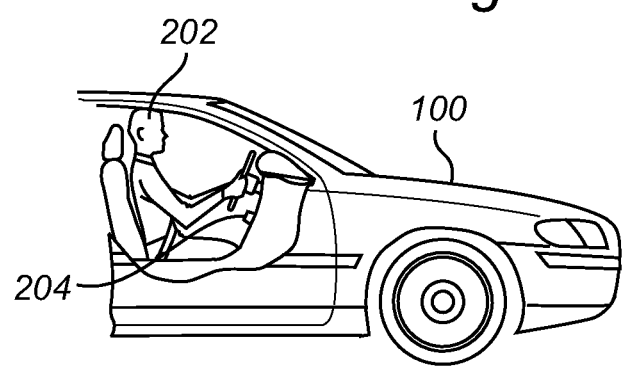
FIG. 2 is a perspective view of the interior of the vehicle, equipped with an internal sensor.
Figure 3:
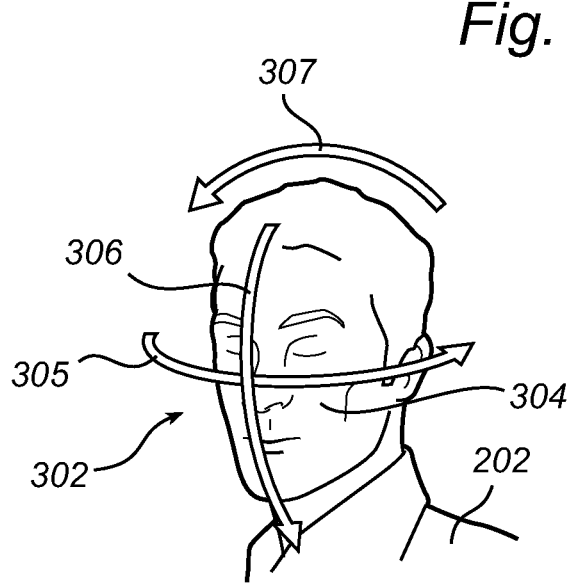
FIG. 3 illustrates a coordinate system of the face of a vehicle operator.

FIG. 2 illustrates an interior of a car 100 including a vehicle operator 202, wherein the car 100 is equipped with an internal sensor, here illustrated as a camera system 204. The camera system 204 is arranged to determine the behavior of the vehicle operator 202 during vehicle operation. Furthermore, the camera system 204 may be calibrated to focus on a predetermined number of positions of the operator's face. These positions may, for example, be the eyes, eye-lids, eyebrows, nose, mouth, cheek, etc. The camera system may be pre-calibrated for a specific operator 202 normally operating the vehicle or being calibrated each time an operator 202 enters the driver seat of the vehicle 100. As the camera system has detected the different positions of the operator's face, an estimation of facial behavior is possible for the camera system. The camera system may hence detect, e.g. head and eye direction, head pose, eye saccade, head-eye saccade, eye closure, speed of eye closure, etc. The camera system may also, by use of a coordinate system 302 in connection to the operator's face 304, illustrated in FIG. 3, detect if the head of the operator is rotating to the right or left (yaw), 305, rotating up or down (pitch), 306, or leaning towards the right or left shoulder (roll), 307. The coordinate system 302 of the face 304 is preferably a polar coordinate system with its origin positioned between the eyes of the operator.

Furthermore, the internal sensors 204 may also, instead of, or additionally to the camera, include other type of operator detecting means. This may, for example, include sensors for detecting EKG or EEG of the operator, steering wheel sensors for detection of steering behavior, sensors in the acceleration pedal and/or braking pedal for detection of inconsistent acceleration and/or braking of the car, sensors in various buttons of the car to detect if, for example, the operator 202 is adjusting any of the various functionalities of the vehicle infotainment system, etc. A still further internal sensor may be a breath analysis sensor or pupil size sensor for detecting intoxication of the operator.

Each object in the vehicle's environment is approximated by a 3D box with target corner points. Input data for objects are received in the following form per object. The data for each target is described in the vehicle-based Cartesian coordinate system and contains corner position (including a standard deviation estimate) for each of the four corners in the X and Y directions, object height (including a standard deviation estimate) in the Z direction, object velocity and object acceleration.

Figure 4A:
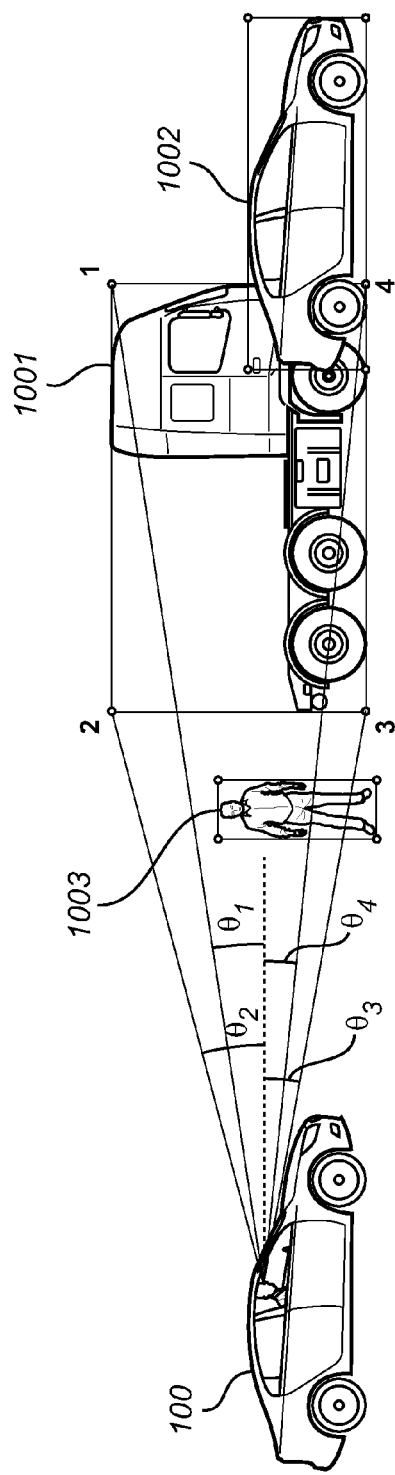
Figure 4B:
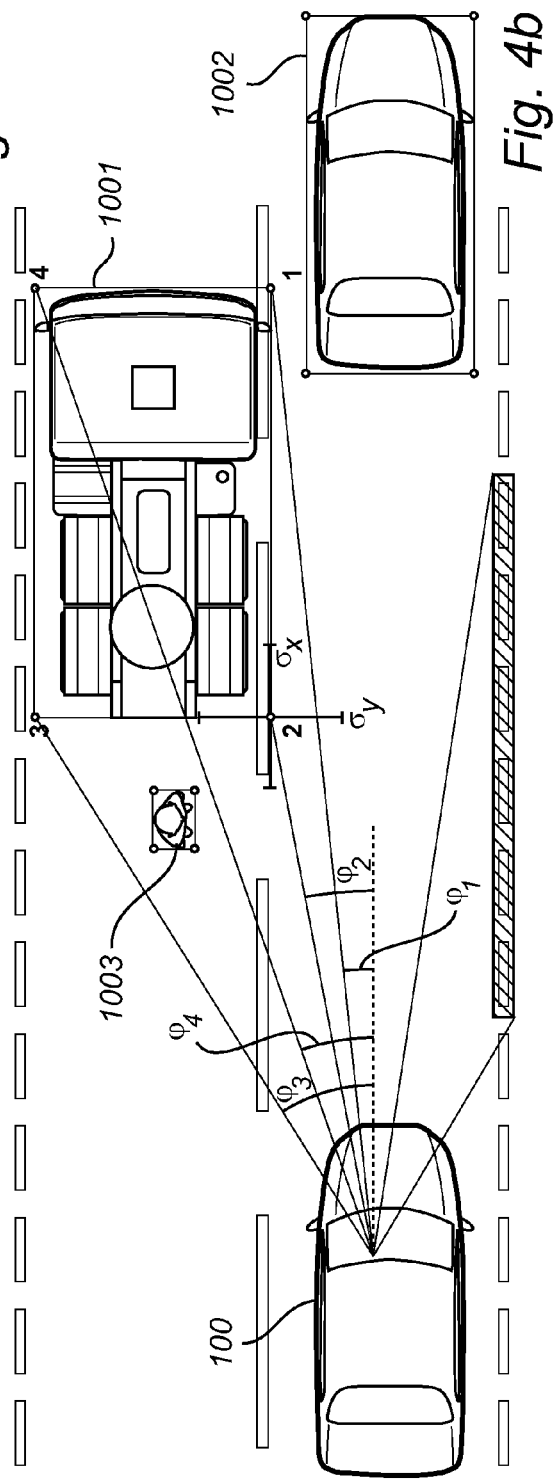

In order to match objects with the driver's vision, the actual 3D world around the driver is divided into three views, a side view, a top view and a driver's view as shown in FIGS. 4a-c, respectively. In FIG. 4c the driver's view is illustrated, comprising a road 1000, a truck 1001, a car 1002, a pedestrian 1003 and lane markings 1004. The side view and the top view are addressed separately to arrive at a description of the environment as seen from the driver's view. In the side and top views, the positions of the surrounding objects are described in the vehicle-based Cartesian coordinate system. This information is combined with the distance from the driver's head to the origin of the vehicle-based coordinate system, to calculate the yaw and pitch angles to the targets in the driver's head-based polar coordinate system.

The yaw ($\phi$) and pitch ($\theta$) angle calculations are done with the following equations:

$$\tan\varphi_1 = \frac{(y_{1,obj} - (y_{DMC} + y_{head}))}{(x_{1,obj} + x_{DMC} + x_{head})} \quad \tan\varphi_2 = \frac{(y_{2,obj} - (y_{DMC} + y_{head}))}{(x_{2,obj} + x_{DMC} + x_{head})}$$

$$\tan\varphi_3 = \frac{(y_{3,obj} - (y_{DMC} + y_{head}))}{(x_{3,obj} + x_{DMC} + x_{head})} \quad \tan\varphi_3 = \frac{(y_{4,obj} - (y_{DMC} + y_{head}))}{(x_{4,obj} + x_{DMC} + x_{head})}$$

In the equations $x_{n,obj}$ and $y_{n,obj}$ is the distance to object corner n in the X and Y directions, respectively and $x_{DMC}$, $y_{DMC}$ and $z_{head}$ is the distance from the origo of the vehicle's coordinate system to the sensor monitoring the driver in the respective directions, and $x_{head}$, $y_{head}$, and $z_{head}$ is the distance between the driver's head and the sensor monitoring the driver in the respective directions.

$$\tan\theta_1 = \frac{(h_{obj} - (z_{DMC} + z_{head}))}{(r_{1,obj} + x_{DMC} + x_{head})} \quad \tan\theta_2 = \frac{(h_{obj} - (z_{DMC} + z_{head}))}{(x_{2,obj} + x_{DMC} + x_{head})}$$

$$\tan\theta_3 = \frac{-(z_{DMC} + z_{head})}{(r_{3,obj} + x_{DMC} + x_{head})} \quad \tan\theta_4 = \frac{-(z_{DMC} + z_{head})}{(r_{4,obj} + x_{DMC} + x_{head})}$$

where $r_{n,obj} = \sqrt{(x_{n,obj}^2 + y_{n,obj}^2)}$ is the distance to object corner n and $h_{obj}$ is the height of the object.

For sake of clarity, this has in FIGS. 4a-b only been illustrated for one of the objects, namely truck 1001. However, the same calculations are used for each object, such as for example the lane markings 1004, vehicles 1002, pedestrians 1003, etc, in the surroundings of the vehicle.

As illustrated in FIG. 4b, with reference to corner point 2 of the truck, the position of the corner points may be approximated by determining confidence intervals based on the signals from the external sensor systems. Confidence intervals are shown in the X and Y directions, and are equally conceivable in the Z direction. The confidence intervals for the corner points may also be expressed in the in the driver's head-based polar coordinate system comprising yaw ($\phi$) and pitch ($\theta$). Furthermore, the method of determining an operator's expectation of a state of an object in the operator's environment may involve using variance computations of the objects corner point in order to determine the objects position. For example, increased variance values imply that the uncertainty of the position of an object is increased which may be accounted for in the determination of the operator's expectation of state of the object.

Figure 6:
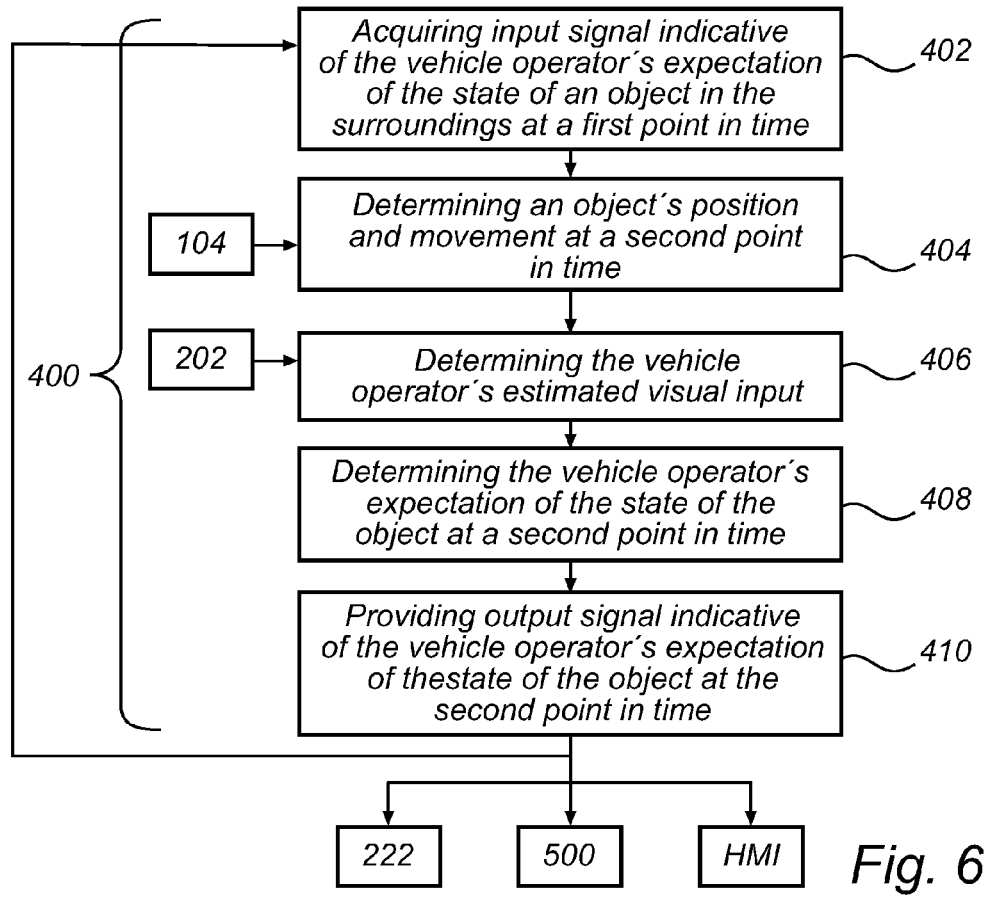
FIG. 6 illustrates a conceptual flow chart of a system according an aspect of the present invention.
Figure 9:
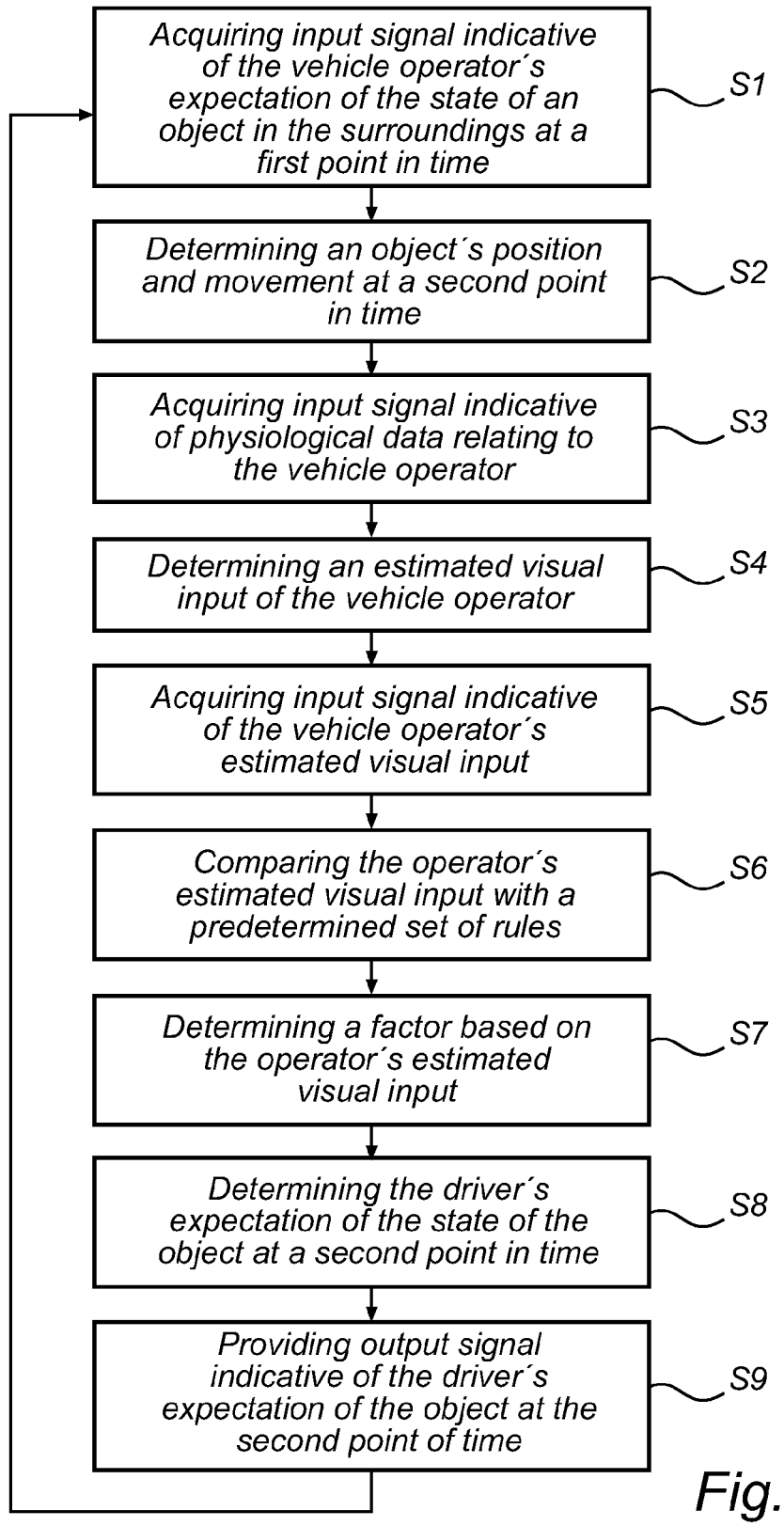
FIG. 9 illustrates a method according to an aspect of the present invention.

Now referring to FIG. 6, which illustrates an embodiment of a system according to the present invention. The method executed by the system is illustrated in FIG. 9. The first system 400 in the illustrated embodiment is a system arranged to determine the driver's expectation of the state, including at least one of the object's position, movement and acceleration, of an object in the driver's surrounding. The system 400 comprises a first subsystem 402 arranged for acquiring an input signal indicative of the driver's expectation of the state of the object at a first point in time, a second subsystem 404 arranged for determining an object's position and movement in the X and Y directions at a second point in time, a third subsystem 406 arranged for acquiring an input signal indicative of the driver's estimated visual input, a fourth subsystem 408 for determining the driver's expectation of the state of the object at the second point in time and a fifth subsystem 410 for providing an output signal indicative of the driver's expectation of the state of the object at the second point in time.

When the system is being used, the first subsystem 402 performs the method step S1 by receiving an input signal indicative of the driver's expectation of the state of an object in the driver's surrounding at a first point in time. The first point in time being prior to the current point in time.

In the second subsystem 404 the method step S2 is performed by determining the object's position and movement in the X and Y directions at a second point in time. The second point in time being the current point in time. The position is calculated using the four object corners as input, whose mean define the center point of the object in each of the X and Y directions. The input is received from the external sensors 104. The object's movement in the X and Y directions is calculated in the same way, only that the corner point velocity is calculated for each of the individual corners as a first step, before taking the mean. A single variance measure of the objects' position or movement may also be calculated by this subsystem, which measure may be utilized by other subsystems later in the process. For example, to obtain this measure, the standard deviation for each corner is first squared, and then the mean of the squared values is calculated to obtain the object's position or movement variance as a single measure.

In the third subsystem 406 an input signal indicative of the estimated visual input of the driver is acquired. The estimated visual input of the driver is based on an input signal from the sensor 202 and may be determined in another estimation system which e.g. outputs a visual input quality value indicative of the operator's level of visual input of the object. For example, the estimated visual input of the operator is determined by acquiring input signal indicative of the physiological data relating to the vehicle operator, in method step S3, determining an estimated visual input of the vehicle operator, in step S4, and acquiring an input signal indicative of the vehicle operator's estimated visual input which corresponds to a visual input quality value, in step S5.

For example, the estimation system may include control means comprising a first input arranged to receive an object position signal indicative of the position of at least one object in the operator's surroundings; and a second input arranged to receive an operator motion input signal indicative of physiological data comprising information relating to at least one of eye, face, head and body motion of the operator of the vehicle, wherein the control means is arranged to estimate an operator eye-gaze direction based on the operator motion input signal, and arranged to determine a visual input quality value representative of level of visual input of the at least one object received by the operator, based on the object position signal and the estimated operator eye-gaze direction. The control means of the system may further arranged to determine an object area associated with the object, such four object corners points, which object area is indicative of the object area of the object as perceived by the operator, wherein the quality value is determined based on the object area. Furthermore, the visual input quality value associated with an object may be estimated by determining an operator eye-gaze distribution indicative of probability for different eye-gaze directions of the operator and/or a visual acuity distribution indicative of visual acuity level of an eye of the operator in relation to a center eye-gaze direction, wherein the eye-gaze distribution and/or visual acuity distribution is e.g. convolved, or integrated, over the object area.

Thereafter, the method step S8 is performed by determining the driver's expectation of the state of the object at the second point in time in the fourth subsystem 408. The driver's expectation of the object's position is determined by weighing together the driver's expectation of the position of the object at the first point in time with the actual position of the object at the second point in time. The weighting factor is variable and is determined in the method step S7. The weighing factor depends on the driver's current visual input of the specific object, which is acquired from the third subsystem 406. In this exemplary embodiment, the weighting factor can vary between 0 and 1, according to a look-up table defined by the user. A high value of visual input, i.e. the driver gives the object much attention, gives a high weighting factor, which means that the driver's expectation will converge towards the correct object position. The opposite, a low visual input value, i.e. the driver does not give the object much attention, will result in that the driver's expectation will be updated according to the driver's last known movement of the object. This means that if the object starts accelerating in some direction while the visual input is low, the driver will not be aware of this and the driver's expectation of the position of the object will correlate worse and worse with the real object position.

The driver's expectation of the object's movements is also done in the fourth subsystem, using the expected position as input. The derivative of the objects position in the driver's expectation is thus the driver's expectation of the object's movements.

In the fifth subsystem 410 the method step S9 is performed. Here, the driver's expectation of the object's position and movement at the second point in time is provided as an output signal that may be sent to e.g. a Human Machine Interface (HMI) or to a second system 500, which will be explained in further detail below, in order to be used as input data in that system. The output signal is also being used as input signal for the first subsystem 402 of the first system 400, for the consecutive point in time.

Figure 7:
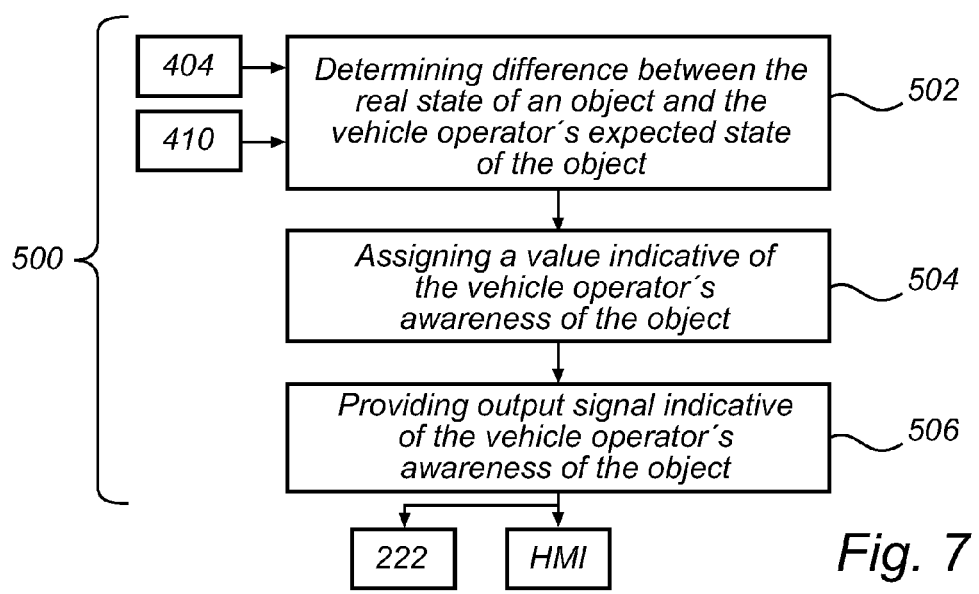
FIG. 7 illustrates a conceptual flow chart of a system according to an aspect of the present invention.
Figure 10:
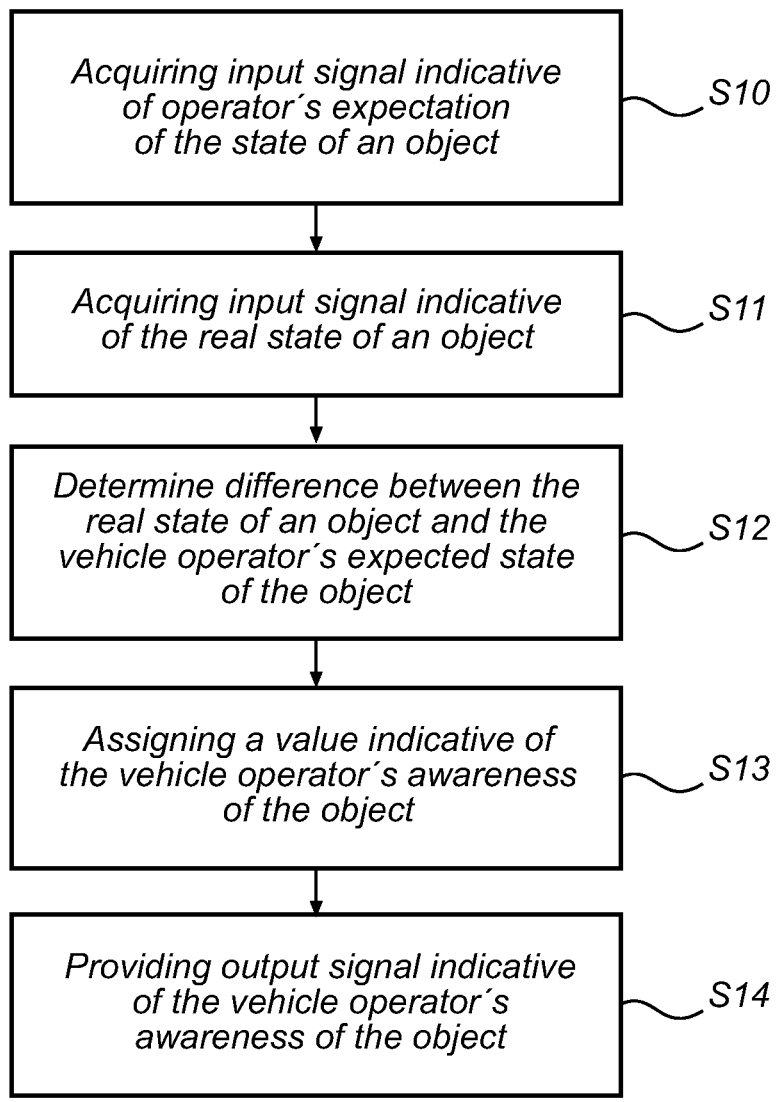
FIG. 10 illustrates a method according to an aspect of the present invention.

In FIG. 7, a second system 500 is illustrated which in the illustrated embodiment is a system arranged to determine the driver's awareness of an object in the driver's surrounding. The method executed by the system is illustrated in FIG. 10. The system 500 comprises a first subsystem 502 for determining the difference between the real state of the object with the driver's expected state of the object, a second subsystem 504 for assigning a value indicative of the driver's awareness of the object and a third subsystem 506 for providing an output signal indicative of the driver's awareness of an object.

In use, the first subsystem 502 performs method step S10 by receiving input data from the second subsystem 404 in the first system 400 in the form of an input signal indicative of the state of an object. The first subsystem 502 also performs method step S11 by receiving input data from the fifth subsystem 410 of the first system 400 in the form of in input signal indicate of the driver's expectation of the state of an object. The input data is thereafter used to execute method step S12 by comparing the object's real position/movement and the driver's expectation of the object's position/movement. The difference between the real position/movement and the driver's expected position/movement is then assessed, both by comparing the actual difference between reality and expectation, i.e. the position difference is measured in meters, the movement difference is measured in meters/second, and by calculating the percentage that the expectation differs from the reality.

In the second subsystem 504, method step S13 is performed by assigning a value to the driver's awareness of an object, based on the difference between the real position/movement and the driver's expectation of the position/movement determined in the first subsystem 502. In this exemplary embodiment, the states are prioritized so that if several of the conditions are true, the one with the lowest value will be chosen as input. In this exemplary embodiment, the following criterions are assigned for the respective levels of awareness: 0—driver does not know object exists; 1—Driver is aware of object existence but has very incorrect understanding of its position; 2—Driver has slightly incorrect understanding of object's position and/or has very incorrect understanding of its motion; 3—Driver has correct understanding of object's position but has slightly incorrect understanding of its motion; 4—Driver's expectation of object's position and motion correlates well with actual position and motion of object.

In the third subsystem 506, method step S13 is performed by providing an output signal indicative of the value determined in the second subsystem 504, i.e. a value indicative of the difference between the real position/movement and the driver's expected position/movement of the object's position and movement at the second point in time is. The output signal may be sent to e.g. a Human Machine Interface (HMI).

The systems 400, 500 have above been described as relating the driver's expectation of the state of an object with the actual state of that object. In reality, the systems 400, 500 perform the same determinations for any relevant object in the driver's environment and provide a respective output signal for each object.

Figure 8A:
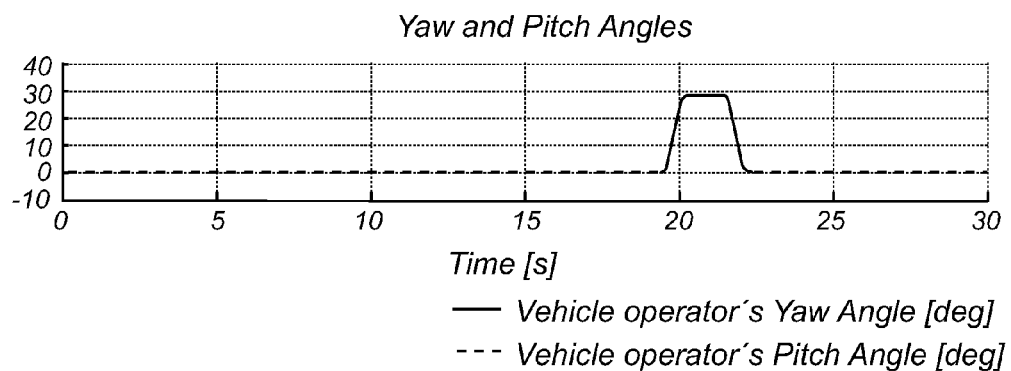
FIGS. 8a-8c schematically illustrates the system of the present invention being used in a driving situation.
Figure 8B:
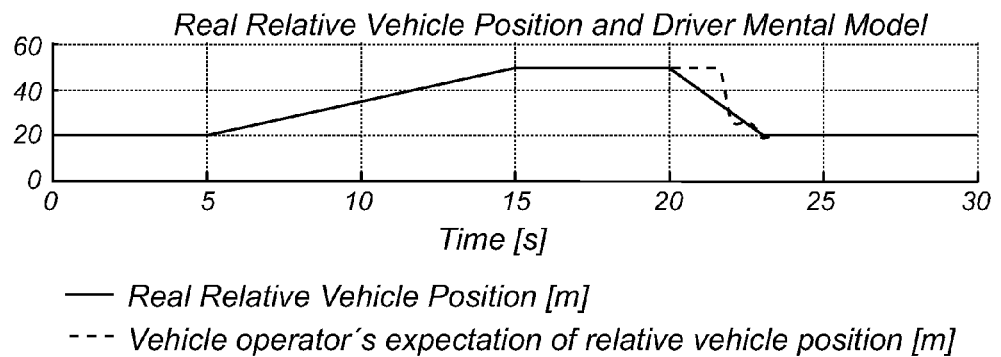
Figure 8C:
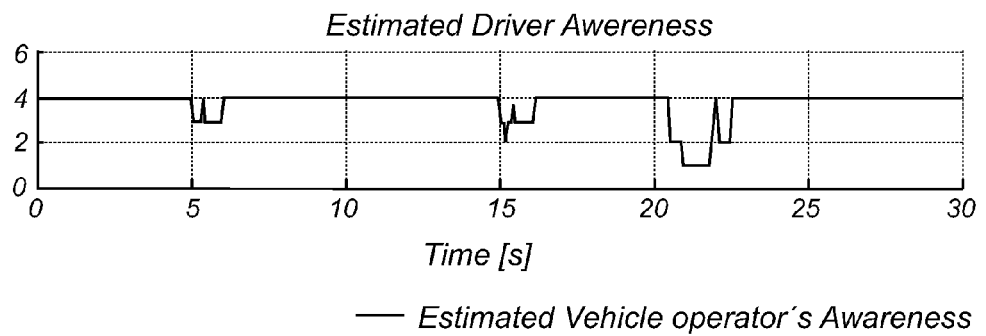

Now turning to FIGS. 8a-c, illustrating an example of the systems 400, 500 in use. FIG. 8a illustrates yaw and pitch angles of a driver for a period of thirty seconds. FIG. 8b illustrates the real relative positions between the driver's vehicle and a vehicle in front of the driver's vehicle and the driver's expectation of the relative positions between the driver's vehicle and the vehicle in front of his vehicle during the same thirty seconds as in FIG. 8a. FIG. 8c illustrates the estimated driver awareness during the same thirty seconds as in FIGS. 8a-b.

In the illustrated example, the driver looks constantly at the lead vehicle until about 19.5 s where he looks away for a few seconds, as seen in the head yaw angle in FIG. 8a. Just after the driver looks away, at about 20 s, the lead vehicle starts to brake, which means that the driver's expectation of the state of the lead vehicle front of his vehicle does no longer correlate well with the real relative vehicle positions. This is also shown in that the driver awareness estimate is rapidly decreased at approximately 21 s. Then, when the driver looks back towards the lead vehicle, the driver's expectation of the state of the lead vehicle is gradually adapting to the real state of that vehicle and the driver awareness estimate is restored to a high level.

It can also be seen in FIGS. 8a-c that at about 5 seconds and 15 seconds the awareness is decreased to 3 even though the driver is constantly looking at the lead vehicle. The reason for this is that it takes a while for the driver to notice the lead vehicle's acceleration and deceleration. At approximately 22 and 23 seconds, the awareness level is changing rapidly, depending on the time it takes for the driver to adjust to the new position and speed of the lead vehicle.

The output signal from either one of the systems 400, 500, i.e. the signal indicative of the operator's expectation of the state of the object at the second point in time or the signal indicative of the difference between the operator's expectation of the state of the object at the second point in time and the state of the object at the second point in time may be used as an input signal to several existing systems 222 in vehicles. For example, in forward collision warning systems, blind spot warning systems and lane departure warning systems, the input signal may be used to adapt the timing of the warning, adapt the level of warnings depending on the driver's awareness level, activate the function automatically even if the driver has shut the system off, or adapt directional warnings. In adaptive cruise control systems, the system may be adapted to adjust to longer distances to leading vehicle when the driver's attention is not on the road, or increase the brake capacity when the driver's expectation of surrounding objects is low. In automatic braking systems, the automatic braking system may be adapted to react earlier if the driver is distracted, as compared to when the driver is well aware of the surrounding traffic. It is of course also conceivable to implement a distraction warning system that warns when the driver's attention to the road and/or surrounding traffic is too low.

To enable faster classification of the driver's attention/awareness of objects that are just coming into range of the sensors monitoring the vehicle surroundings the concept of zones can be useful. By defining zones around the vehicle, is possible to estimate the driver's attention/awareness of objects in that zone, even if the sensors have not discovered an object yet. Then, when the sensors do discover it, the estimated driver attention/awareness can be assigned to the object directly, instead of giving an unknown attention/awareness of that object.

Figure 5:
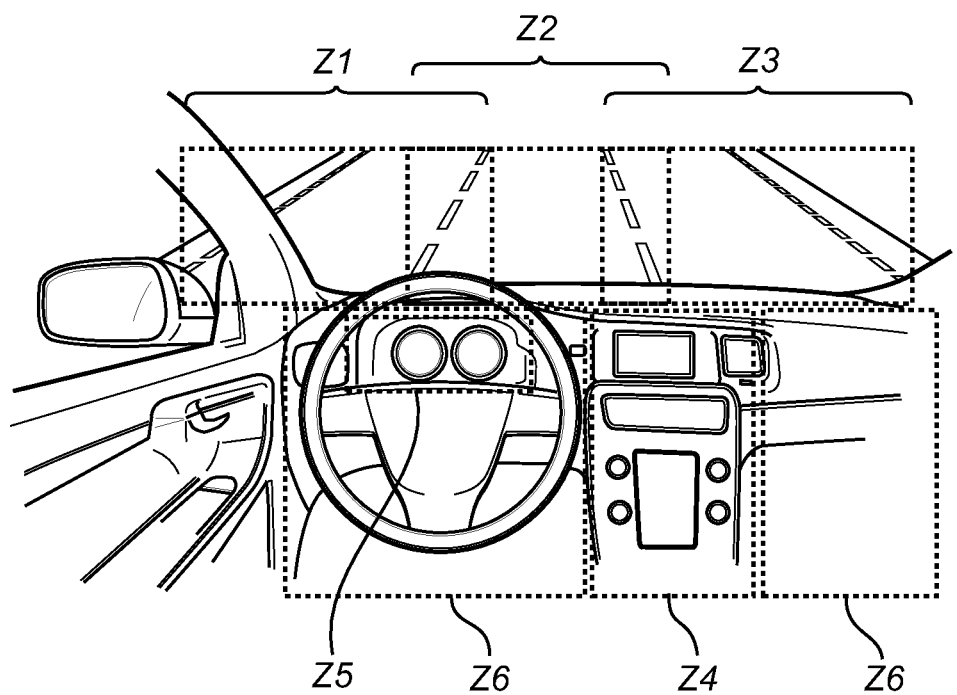
FIG. 5 illustrates an example of how zones ahead of and inside the vehicle may be defined.

Zones are defined as 3D objects, like any other object around, or inside, the vehicle. FIG. 5 shows an example of how zones ahead of and inside the vehicle could be defined. However, the figure only shows 2D objects (no X component) for simplicity in the visualization. The zones in FIG. 5 are just examples of how zones can be used, for some applications, zones at the side or rear of the vehicle can be useful.

Zones may often overlap each other in the driver's view. An object may also be present in several zones at the same time. In such cases, the driver attention/awareness of the different zones should be weighed together, depending on how much of the object that is present in each zone, when assigning the driver's attention/awareness to an appearing object.

Even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims.

For example, the choice of five levels of awareness is for illustrative purposes only and other numbers of levels are conceivable.

Further, the invention is not limited to the use of a camera and/or radar sensor for detecting the environment of the vehicle; other known and suitable sensors are of course also conceivable.

In the described embodiment, all object types are being handled in the same manner in the systems. However, it might be suitable to provide for different determination systems depending on the type of object, different object types do not necessarily exhibit the same type of movement patterns.

Furthermore, it is also conceivable to include confidence calculations in the system 500. This could e.g. be done by calculating "optimistic"/"pessimistic" awareness estimates and compare these with the normal awareness estimate to see how much they differ. The optimistic awareness estimate may be achieved through adding some value (e.g. one standard deviation) to the vehicle operator's estimated visual input and calculate what the awareness would become using this "optimistic" awareness estimate. Analogously, the pessimistic awareness estimate may be obtained by subtracting the same value (e.g. one standard deviation) from the vehicle operator's estimated visual input value and then calculating the resulting "pessimistic" awareness estimate. The more the estimates would differ, the lower the awareness confidence would be, since a large standard deviation for the vehicle operator's estimated visual input means that the estimate is uncertain and that the awareness estimate will then be uncertain as well.

Furthermore, in the claims, the word "comprising" does not exclude other elements or steps, and the indefinite article "a" or "an" does not exclude a plurality.

The invention claimed is:

1. A method for determining a vehicle operator's expectation of a state of an object in the operator's environment, the method comprising:
  acquiring an input signal indicative of the operator's expectation of the state of the object at a first point in time;
  determining a state of the object at a second point in time based on an input signal indicative of the state of the object, the second point in time being later than the first point in time;
  acquiring an input signal indicative of an estimated visual input of the operator at the second point in time;
  determining the operator's expectation of the state of the object at the second point in time, based on the operator's expectation of the state of the object at the first point in time, the estimated visual input of the operator of the vehicle at the second point in time and the state of the object at the second point in time; and
  providing an output signal indicative of the difference between the operator's expectation of the state of the object at the second point in time and the state of the object at the second point in time.

2. A method according to claim 1, wherein the state of the object includes at least one of the position of the object, the movement of the object, and the acceleration of the object.

3. A method according to claim 1, wherein the input signal indicative of an estimated visual input of the operator at the second point in time is determined based on an input signal indicative of physiological data comprising information relating to at least one of eye, face and body motion of the operator of the vehicle.

4. A method according to claim 1, further comprising:
  determining a factor by which the operator's expectation of the state of the object at the first point in time and the state of the object at the second point in time should be weighed when determining the operator's expectation of the state of the object at the second point in time,
  wherein the factor is determined by:
  comparing the operator's estimated visual input of the object at the second point in time with a set of rules.

5. A system for determining a vehicle operator's expectation of a state of an object in the vehicle operator's environment, the system comprising:
  a processor configured to,
    acquire an input signal indicative of the operator's expectation of the state of the object at a first point in time,
    determine a state of the object at a second point in time based on an input signal indicative of the state of the object, the second point in time being later than the first point in time,
    acquire an input signal indicative of an estimated visual input of the operator at the second point in time,
    determine the operator's expectation of the state of the object at the second point in time, based on the operator's expectation of the state of the object at the first point in time, the estimated visual input of the operator of the vehicle at the second point in time and the state of the object at the second point in time, and
    provide an output signal indicative of the difference between the operator's expectation of the state of the object at the second point in time and the state of the object at the second point in time.

6. A system according to claim 5, wherein the state of the object includes at least one of the position of the object, the movement of the object and the acceleration of the object.

7. A system according to claim 5, wherein the processor is configured to determine an estimated visual input of the operator at the second point in time, based on an input signal indicative of physiological data comprising information relating to at least one of eye, face and body motion of the operator of the vehicle.

8. A system according to claim 5, wherein the processor is configured to
  determine a factor by which the operator's expectation of the state of the object at the first point in time and the state of the object at the second point in time should be weighed when determining the operator's expectation of the state of the object at the second point in time, wherein the factor is determined by:
  the processor comparing the operator's estimated visual input of the object at the second point in time with a set of rules.

9. A system according to claim 5, wherein the input signal indicative of physiological data comprising information relating to at least one of eye, face and body motion of the operator of the vehicle is generated by an image sensor monitoring the operator.

10. A system according to claim 5, wherein the input signal indicative of the state of an object is provided by a sensor.

11. A system according to claim 5, wherein the input signal indicative of the state of an object is provided by an object-to-vehicle communication device.

12. A non-transitory computer readable medium embodying a computer program product for determining a vehicle operator's expectation of a state of an object in the operator's environment, the computer program product comprising code configured to, when executed by a processor, cause the processor to:

acquire an input signal indicative of the operator's expectation of the state of the object at a first point in time;

determine a state of the object at a second point in time based on an input signal indicative of the state of the object, the second point in time being later than the first point in time;

acquire an input signal indicative of an estimated visual input of the operator at the second point in time;

determine the operator's expectation of the state of the object at the second point in time, based on the operator's expectation of the state of the object at the first point in time, the estimated visual input of the operator of the vehicle at the second point in time and the state of the object at the second point in time; and provide an output signal indicative of the difference between the operator's expectation of the state of the object at the second point in time and the state of the object at the second point in time.

* * * * *